US00PP29607P2

(12) United States Plant Patent
Trees

(10) Patent No.: US PP29,607 P2
(45) Date of Patent: Aug. 21, 2018

(54) ***CESTRUM* PLANT NAMED 'GOLD NIGHT'**

(50) Latin Name: *Cestrum nocturnum*
Varietal Denomination: Gold Night

(71) Applicant: The Conard-Pyle Company, West Grove, PA (US)

(72) Inventor: Scott C. Trees, Arroyo Grande, CA (US)

(73) Assignee: The Conard-Pyle Company, West Grove, PA (US)

( * ) Notice: Subject to any disclaimer, the term of this patent is extended or adjusted under 35 U.S.C. 154(b) by 43 days.

(21) Appl. No.: 15/530,659

(22) Filed: Feb. 16, 2017

(51) Int. Cl.
*A01H 5/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Karen M Redden
(74) *Attorney, Agent, or Firm* — Audrey Charles

(57) ABSTRACT

A new and distinct cultivar of *Cestrum* plant named 'Gold Night', characterized by its medium yellow-colored flowers, dark green-colored foliage, and moderately vigorous, upright and outwardly spreading growth habit, is disclosed.

1 Drawing Sheet

Latin name of genus and species of plant claimed: *Cestrum nocturnum.*

Variety denomination: 'Gold Night'.

BACKGROUND OF THE INVENTION

The present invention relates to a new and distinct cultivar of *Cestrum* plant botanically known as *Cestrum nocturnum* and hereinafter referred to by the cultivar name 'Gold Night'.

The new cultivar originated in a controlled breeding program in Guadalupe, Calif. during May 2010. The objective of the breeding program was the development of *Cestrum* cultivars having early continuous flowering and upright, well-branched habits.

The new *Cestrum* cultivar is the result of open-pollination. The female (seed) parent of the new cultivar is *Cestrum nocturnum* common species form, not patented, characterized by its light greenish-yellow colored flowers, medium green-colored foliage, and vigorous, upright growth habit. The male (pollen) parent of the new cultivar is unknown. The new cultivar was discovered and selected as a single flowering plant within the progeny of the above stated open-pollination during August 2011 in a controlled environment in Guadalupe, Calif.

Asexual reproduction of the new cultivar by terminal stem cuttings since December 2011 in Guadalupe, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Gold Night' as a new and distinct cultivar of *Cestrum* plant:

1. Medium yellow-colored flowers;
2. Dark green-colored foliage; and

3. Moderately vigorous, upright and outwardly spreading growth habit.

Plants of the new cultivar differ from plants of the female parent primarily in having a different flower color, darker foliage and reduced growth vigor.

Of the many commercially available *Cestrum* cultivars, the most similar in comparison to the new cultivar is *Cestrum* 'Orange Peel', not patented. However, in comparison, plants of the new cultivar differ from plants of *Cestrum* 'Orange Peel' in at least the following characteristic:

1. Plants of the new cultivar have a flower color different from plants of *Cestrum* 'Orange Peel'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Gold Night'. The plants were grown in 3-gallon containers for three years in an outdoor nursery in Guadalupe, Calif. Plants were pruned two times each year to remove approximately one-third growth. In early December 2016, the plants were transplanted to 5-gallon containers in West Grove, Pa. and held under greenhouse conditions.

DETAILED BOTANICAL DESCRIPTION

Figure 1:
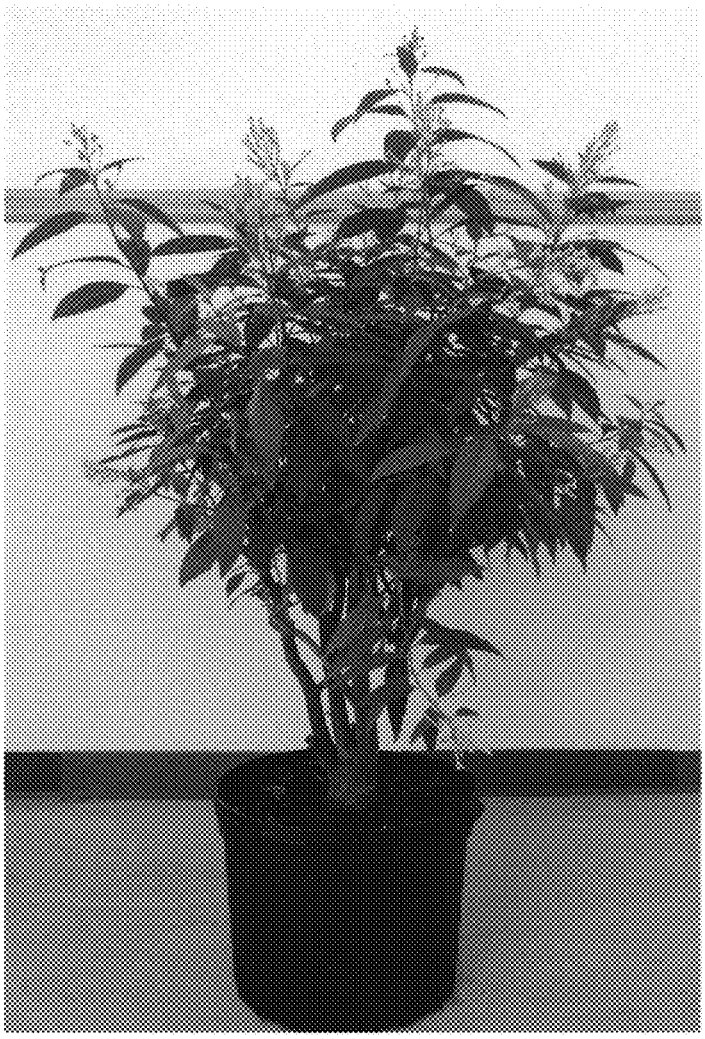
FIG. 1 illustrates a side view of the overall growth and flowering habit of 'Gold Night'.
Figure 2:
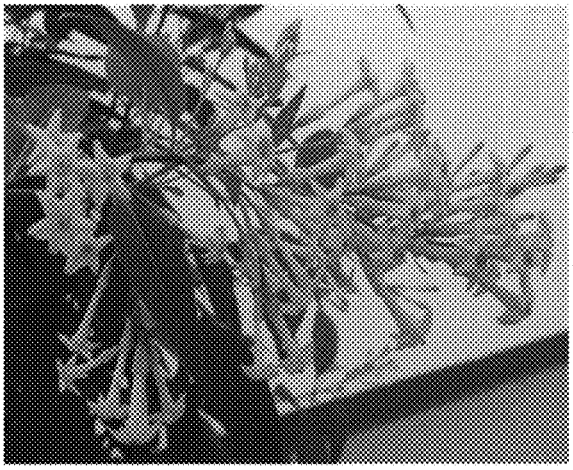
FIG. 2 illustrates a dose-up view of a flower cluster of 'Gold Night'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in December, 2016 under natural light conditions in West Grove, Pa.

The following descriptions and measurements describe plants produced from cuttings from stock plants. The plants were grown in 3-gallon containers utilizing a soilless growth medium for three years in an outdoor nursery in Guadalupe, Calif. Plants were pruned two times each year to remove approximately one-third growth. In early December 2016, the plants were transplanted to 5-gallon containers in West Grove, Pa. and held under greenhouse conditions to flower. Greenhouse temperatures were maintained at 74° F. to 80° F. (23° C. to 27° C.) during the day and approximately 66° F. to 70° F. (19° C. to 21° C.) during the night. Greenhouse light levels of 2,200 footcandles to 3,100 footcandles were maintained during the day. Measurements and numerical values represent averages of typical plants.

Botanical classification: *Cestrum nocturnum* cultivar Gold Night.

Parentage:

*Female parent*.—*Cestrum nocturnum* common species form, not patented.

*Male parent*.—Unknown.

Propagation:

*Type cutting*.—Terminal cuttings.

*Time to initiate roots*.—Approximately 7 to 10 days.

*Time to produce a rooted cutting*.—Approximately 4 to 5 weeks.

*Root description*.—Fibrous and fine; white to brown in color.

*Rooting habit*.—Freely branching; dense.

Plant description:

*Commercial crop time*.—Approximately 3 to 4 months from a rooted cutting to finish in a one-gallon container.

*Growth habit and general appearance*.—Shrub, moderately vigorous, upright and outwardly spreading growth habit.

*Hardiness*.—USDA Zone 8 (10° F. to 20° F.).

*Heat tolerance*.—Regularly tolerates temperatures as high as 40.6° C. (105° F.) in the summer.

*Size*.—Height from soil level to top of plant plane: Approximately 80.0 cm. Width: Approximately 50.0 cm.

*Branching habit*.—Freely branching. Pinching not required. Aspect: Erect to 45° from center. Quantity of branches per plant: Approximately 5 main stems per plant with approximately 5 lateral branches per stem.

*Lateral branches*.—Strength: Strong. Length: Approximately 30.0 cm long. Diameter: Approximately 4.0 mm. Length of central internode: Approximately 1.5 cm. Texture of mature stem: Woody. Color of young stems: 143B. Color of mature stems: 199B.

Foliage description:

*General description*.—Form: Simple. Arrangement: Alternate. Fragrance: None detected.

*Leaves*.—Aspect: Perpendicular to stem. Shape: Oblanceolate. Margin: Entire. Apex: Acute. Base: Cuneate. Venation pattern: Pinnate. Length of mature leaf: Approximately 12.0 cm. Width of mature leaf: Approximately 4.5 cm. Texture of upper surface: Glabrous. Texture of lower surface: Glabrous, ribbed. Color of upper surface of young and mature foliage: NN137A with venation color of 138B. Color of lower surface of young and mature foliage: 138B with venation color of 138B.

*Petiole*.—Length: Approximately 8.0 mm. Diameter: Approximately 2.0 mm. Texture: Glabrous. Color of upper and lower surfaces: 138B.

Flowering description:

*Flowering season*.—'Gold Night' is free flowering under outdoor growing conditions with substantially continuous blooming from spring through autumn and year-round in a greenhouse environment.

*Lastingness of individual inflorescence on the plant*.—Approximately 10 days.

*General description*.—Compound corymbs. Aspect: Facing upward to outward. Fragrance: Slight, sweet in evening. Quantity per plant: Approximately 30. Diameter: Approximately 6.0 cm. Height: Approximately 9.0 cm.

*Peduncle*.—Strength: Strong. Shape: Rounded. Aspect: Erect to about 45° from branch axis. Length: Approximately 2.0 cm. Diameter: Approximately 2.0 mm. Texture: Glabrous. Color: 144A.

Flower description:

*General description*.—Type: Salverform.

*Bud*.—Rate of opening: Generally takes 7 to 10 days for bud to progress from first color to fully open flower.

*Bud just before opening*.—Shape: Tubular. Length: Approximately 1.8 mm. Diameter: Approximately 5.0 mm. Color: Tube portion 5A, petal lobes closest to 151C.

*Corolla*.—Depth: Approximately 1.7 cm. Diameter: Approximately 1.5 cm.

*Petals*.—Quantity: 5, non-imbricate. Petals are fused at base forming a corolla tube. Shape: Obovate. Appearance: Dull. Aspect: Flat. Margin: Entire. Apex: Acute. Length from throat: Approximately 6.0 mm. Width: Approximately 4.0 mm. Texture of upper surface: Glabrous. Texture of lower surface: Glabrous. Color of upper surface when first and fully open: 7B. Color of lower surface when first and fully open: 7B.

*Corolla tube*.—Length: Approximately 1.5 cm. Diameter at tube opening: Approximately 5.0 mm. Diameter at base: Approximately 2.0 mm. Texture of inner surface: Glabrous. Texture of outer surface: Glabrous. Color of inner surface: 7B. Color of outer surface: 7B.

*Calyx*.—Shape: Tubular. Length: Approximately 6.0 mm. Diameter at tip: Approximately 2.0 mm. Diameter at base: Approximately 2.0 mm. Texture of inner surface: Glabrous. Texture of outer surface: Glabrous. Color of inner surface: 145B. Color of outer surface: 145A with highlights of near 184B around margin and apex.

*Pedicel*.—Strength: Strong. Aspect: Erect. Length: Approximately 0.5 cm to 1.0 cm. Diameter: Approximately 1.0 mm. Texture: Glabrous. Color: 144B.

*Reproductive organs*.—Androecium: Stamen quantity: 5 per flower. Stamen length: Approximately 9.0 mm. Anther shape: Rounded. Anther length: Less than 1.0 mm. Anther color: 160A. Pollen amount: Moderate.

Pollen color: 163A. Gynoecium: Pistil quantity: 1 per flower. Pistil length: Approximately 1.8 mm. Stigma shape: Discoid. Stigma length: Less than 1.0 mm. Stigma color: 143A. Style length: Approximately 1.8 mm. Style color: 145C. Ovary diameter: Less than 1.0 mm. Ovary color: N144C.

Seed and fruit production: Neither seed nor fruit production has been observed.

Disease and pest resistance: Resistance to pathogens and pests common to *Cestrum* has not been observed.

What is claimed is:

1. A new and distinct cultivar of *Cestrum* plant named 'Gold Night', substantially as herein illustrated and described.

* * * * *